United States Patent [19]
Hoogendijk et al.

[11] Patent Number: 6,096,274
[45] Date of Patent: Aug. 1, 2000

[54] ANALYSIS DEVICE

[75] Inventors: Robert Hoogendijk, Ridderkerk; Willem Boor, Waalwijk, both of Netherlands

[73] Assignee: Applikon B.V., Schiedam, Netherlands

[21] Appl. No.: 09/089,667

[22] Filed: Jun. 3, 1998

[30] Foreign Application Priority Data

Jun. 3, 1997 [NL] Netherlands ................ 1006211

[51] Int. Cl.⁷ ................................................. G01N 21/79
[52] U.S. Cl. ............................................. 422/75; 436/51
[58] Field of Search ................... 422/67, 75, 81; 436/51

[56] References Cited

U.S. PATENT DOCUMENTS

| | | |
|---|---|---|
| 4,155,978 | 5/1979 | Naono et al. . |
| 4,715,237 | 12/1987 | Kaempf et al. . |
| 5,192,509 | 3/1993 | Surjaatmadja et al. .......... 436/51 |
| 5,340,541 | 8/1994 | Jackson et al. .................. 436/51 |
| 5,389,546 | 2/1995 | Becket ............................. 436/51 |

FOREIGN PATENT DOCUMENTS

| | | | |
|---|---|---|---|
| 8903036 | 4/1989 | WIPO | ................. 436/51 |
| WO 96/31782 | 10/1996 | WIPO . | |

OTHER PUBLICATIONS

Jaromir Ruzicka et al., "Sequential injection: a new concept for chemical sensors process analysis and laboratory assays", pp. 329–343, Analytica Chimica Acta., vol. 237, 1990.

*Primary Examiner*—Jeffrey Snay
*Attorney, Agent, or Firm*—Young & Thompson

[57] ABSTRACT

The invention relates to an analysis device with a multi-way valve which is connected, via a pump line, to a bidirectional pump. A storage member for storing a sample fed to it and any auxiliary substances is accommodated in the pump line. The multi-way valve is connected, via two separate discharge lines, to an analysis vessel. The multi-way valve and the pump are controlled, with the aid of a microprocessor, in such a manner that the following steps are carried out:

a. connecting a first feed line to the pump line via the multi-way valve, in order to feed sample to the storage member,
  b. using the pump to suck the sample into the storage member,
  c. connecting the pump line, via the multi-way valve, to a first discharge line which opens into the analysis vessel,
  d. feeding some of the sample present in the storage member to the analysis vessel via the pump and via the first discharge line,
  e. connecting the pump line to the flushing line via the multi-way valve,
  f. discharging sample which has remained in the storage member via the flushing line by feeding the reactant to the multi-way valve until the multi-way valve is full of reactant,
  g. connecting the pump line, via the multi-way valve, to a second discharge line which opens into the analysis vessel, and
  h. introducing the reactant into the analysis vessel via the second discharge line.

7 Claims, 2 Drawing Sheets

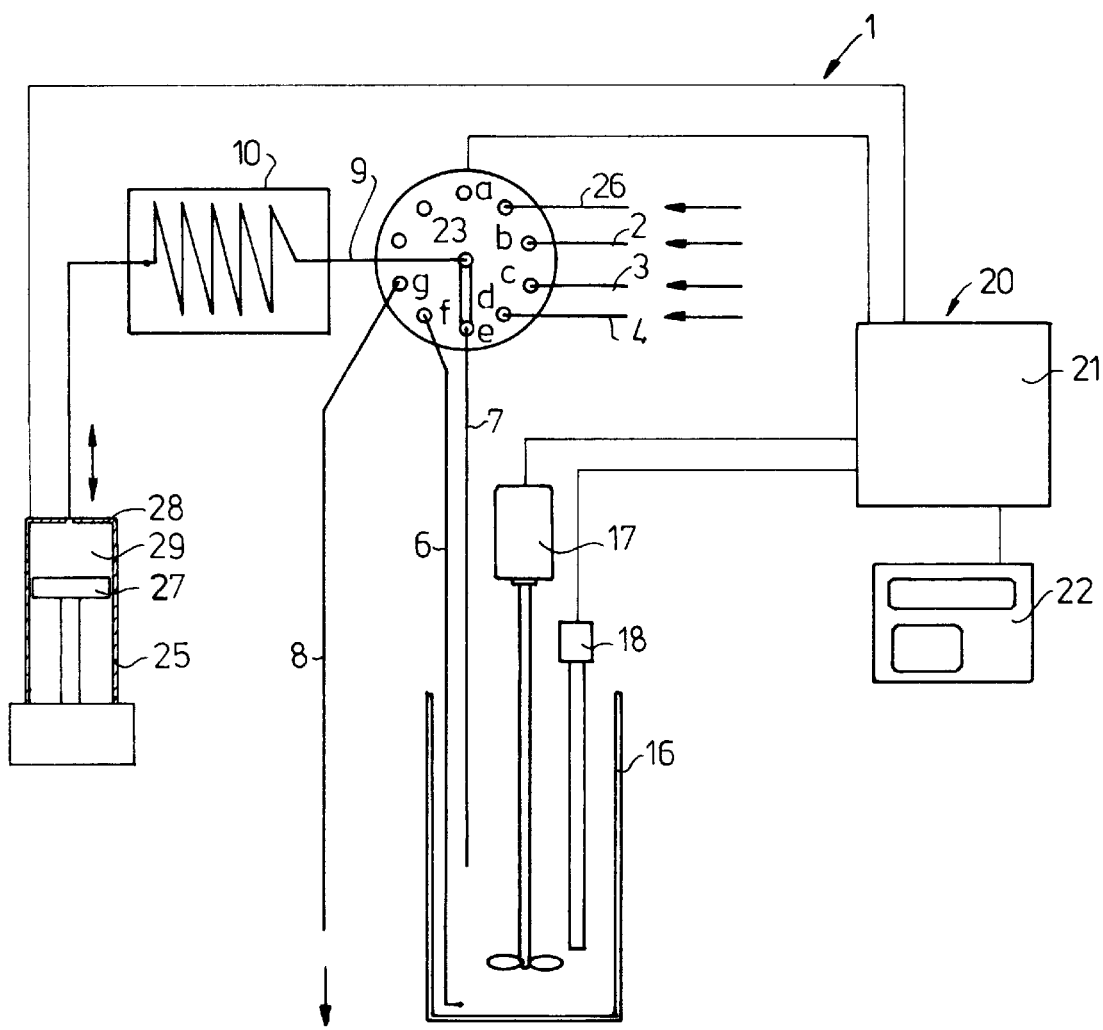

ANALYSIS DEVICE

BACKGROUND OF THE INVENTION

The invention relates to an analysis device provided with a pump which is connected, via a pump line, to a multi-way valve, a first and second discharge line, which are connected to the multi-way valve and can be connected to the analysis vessel, a first feed line, which is connected to the multi-way valve, for feeding a sample to be analysed to the multi-way valve, a second feed line, which is connected to the multi-way valve or to the pump, for feeding a reactant to the multi-way valve, a flushing line which is connected to the multi-way valve, it being possible to place the discharge lines, the first feed line and the flushing line in fluid communication with the pump line via the valve, as well as an operating device for controlling the pump and the multi-way valve.

DESCRIPTION OF THE RELATED ART

An analysis device of this kind is known from U.S. Pat. No. 4,715,237. FIG. 11 of the American patent shows an analysis device in which a reagent and a liquid to be analysed can be received from separate containers in a piston pump. To this end, the entry opening of the pump is provided with a multi-way valve, which is connected, via respective lines, to the containers for the reagent, for an auxiliary solution, and to a container for the substance to be analysed. The mixture of the substance to be analysed and the reagent can then be fed by the piston of the pump, via the multi-way valve, to a measuring cell, where the concentration of ions can be determined with the aid of a system of electrodes.

The prior art also reveals devices for so-called wet-chemical analysis methods, in particular for titrimetric analysis methods and for standard addition methods. These known devices can be used to carry out automatic analyses which are controlled with the aid of a microprocessor system which can be operated and programmed via a control panel or keyboard. The simplification which devices of this kind represent is important primarily for a process analysis system which can analyse liquid samples completely automatically, many times in succession.

In a conventional configuration, a titration is carried out in a small reaction vessel into which a specific quantitative amount of liquid sample is transferred. Then, in the case of a titrimetric analysis method, a reactant (titrant) is added to this liquid with constant mixing, and the progress of the reaction is monitored using a sensor, for example a pH electrode. From the progress of the reaction, it is possible to calculate the concentration of a defined substance in the sample (for example the concentration of acid) on the basis of the consumption of titrant (for example base). In this case, use is made of so-called equivalence points in the progress of the reaction, at which the quantity of substance to be determined in the sample is equal to the quantity of titrant added.

In the known devices, a first pump is used to transfer a defined quantity of sample into a small reaction vessel. Then, a second pump is used to add titrant while the mixture is being stirred with an agitator. The pumps may comprise a burette, out of which the liquid is pressed using a plunger. In this case, a valve is then used, via which the burette can be refilled or with which the burette can meter liquid into the reaction vessel. A pump system of this kind is generally better able to meet the required accuracy with which the additions have to be performed.

If appropriate, prior to the titration one or more additional reagents may be added via another separate pump in order to create a chemical medium in the solution in which the intended reaction between the sample and the titrant will proceed (better) or which makes the reaction more specific for the substance to be analysed. Also, an auxiliary reagent may, for example, be used to perform a so-called back titration, in which the substance to be analysed in the sample reacts with the reagent, and the resulting product is titrated with titrant. From this consumption, it is possible to derive the concentration of the substance to be determined in the sample. The progress of the reaction is monitored by means of a sensor which is read by the microprocessor system. On the basis of this signal, the titrant pump is activated so that a titration curve from which the equivalence point can be derived is produced. The microprocessor system carries out all the calculations which are required to do this. In addition, it activates a valve of the discharge line of the vessel and all the pumps. After the ultimate concentration of the substance to be determined in the sample has been calculated, the reaction vessel is flushed with a rinsing agent supplied by means of a further pump. Before this is done, the vessel is emptied via the valve in the discharge line. The rinsing agent is also removed in this way. The flushing step in this method is not imperative, but does improve the accuracy with which subsequent analyses are carried out. When the reaction vessel is emptied, it is inevitable that a small quantity of reactant will remain behind, which will have an adverse effect on the next analysis. The flushing step therefore prevents this, since the rinsing agent itself does not have any adverse effect, which is virtually always true if the correct solvent is selected.

The microprocessor system carries out this sequence a number of times using one or more different flows of sample. In the latter case, it is necessary to configure more pumps so as to transfer the samples to the vessel, or else it is necessary to use another multi-channel sample collection system. The sequence can be programmed, started and stopped with the aid of an input member of the microprocessor. It is also possible to program and carry out different sequences or programmes. For example, in addition to analysing samples it is also possible to analyse a standard, which can be used to check whether the configuration is functioning correctly since the result of an analysis performed on a standard is established in advance. Also, a calibration liquid can be used in this way to calibrate the concentration of the titrant.

The installation which is known from American patent U.S. Pat. No. 4,715,237 has the drawback that the various liquids in the burette or piston are drawn up in order subsequently to be metered. This can cause cross-contamination between the various liquids. If the system described in U.S. Pat. No. 4,715,237 is used to draw up titrant and to meter it into the reaction vessel with the desired accuracy, a small quantity of this liquid will remain behind in the connecting hoses and in the burette itself during the prior operation of placing a quantity of sample and, if appropriate, reagent in the vessel by means of the burette. As a result, the titrant may be contaminated on use. Then, after analysis, the sample which is drawn up again will be contaminated by the titrant which has remained in the system. As a result, the accuracy of the analysis is limited.

In the known systems, in which a separate pump is used for each line for the reactant, the reagent, the rinsing agent and the sample, it is true that there is no contamination, but on the other hand these devices are relatively complex. One object of the present invention is therefore to provide an analysis device of simple design in which accurate analyses can be carried out without contamination.

SUMMARY OF THE INVENTION

To this end, the analysis device according to the present invention is characterized in that a storage member is positioned in the pump line for receiving the sample to be analysed, the operating device being designed to successively receive the sample in the storage member, transfer the sample, via the first discharge line, from the storage member into the analysis vessel and transfer the reactant, via the second discharge line, into the analysis vessel.

By accommodating a storage member in the pump line, for example in the form of a coil-shaped line part, the sample to be analysed can be collected therein with the aid of the single pump. Then, some of the sample to be analysed can be fed from the storage member, via a separate discharge line, to the analysis vessel or reaction vessel, so that an uncontaminated quantity of sample is obtained. Subsequently, the remainder of the sample which adjoins the reactant present in the pump line can be discharged via the flushing line. Then, the reactant can be fed, via the pump line, to the multi-way valve and added, via a separate, second feed line, to the analysis vessel in a metered manner.

According to one embodiment, the reactant may be fed to the pump from a container situated upstream of the pump. According to a second embodiment according to the invention, the pump may comprise a storage reservoir for the reactant and may, for example, be designed as a burette. Via the multi-way valve, a supply of reactant can be fed to the storage reservoir of the pump. With a design of this kind, it is also possible to accommodate air in the storage reservoir of the pump. The sample and the reactant can then be introduced in succession into the analysis vessel via the storage member and along separate discharge lines and, after an analysis has been completed, all the contents of the analysis vessel can be accommodated in the storage member. Finally, the entire storage member as well as the pump line can be emptied by driving out the air present in the pump. In this case, a separate flushing line can be dispensed with and the mixture of substances analysed can be discharged via, for example, the sample feed line. However, a drawback of a system of this kind is that the air in the storage reservoir of the pump is compressible, with the result that metering of sample and reactant is less accurate.

The simplified analysis device according to the present invention is extremely flexible with regard to various applications. In addition to titrations, it is also possible to use standard addition methods in which use is generally made of ion selective electrodes as the sensor. Instead of titrant, the pump can then pump a standard solution which is added in a defined quantity to the sample. It is also possible to carry out direct measurements in, for example, photometric analyses. In that case, reagents are added to the sample, resulting in a specific colour complex. The intensity of the colour represents a measurement of the concentration of the substance to be analysed in the sample, and this is measured using a photometric sensor. In addition to various analysis methods, the configuration can also easily be adapted with regard to the number of sample streams which are to be analysed and the number of reagents used for this without having to change the basic equipment. The abovementioned back titration and a calibration sequence can also be carried out without change. It would even be possible to combine various methods if a plurality of sensors are placed in the reaction vessel. The options are restricted only by the number of connections to the multi-way valve.

It should be pointed out that the use of a storage container in the form of a reactor coil in the pump line for devices for so-called sequential injection analysis has been described in Analytica Chimica Acta, 237 (1990) 329–343, Elsevier Science Publishers B.V., Amsterdam. In this case, however, the sample to be analysed and the reactant are drawn into the reactor coil together and the progress of the reaction is measured using a sensor accommodated in the pump line, for example a pH sensor or a flow cell. In contrast to the analysis device according to the present invention, the flow injection method described makes use of reproducible concentration gradients and measurements of the reactions at their transition surface in the reactor coil.

BRIEF DESCRIPTION OF THE DRAWINGS

A number of embodiments of an analysis device according to the present invention will be described in more detail by way of example with reference to the appended drawing, in which:

FIG. 2 shows a second embodiment of an analysis device according to the present invention, with the feed line for the reactant opening into the multi-way valve.

DESCRIPTION OF THE PREFERRED EMBODIMENTS

Figure 1:
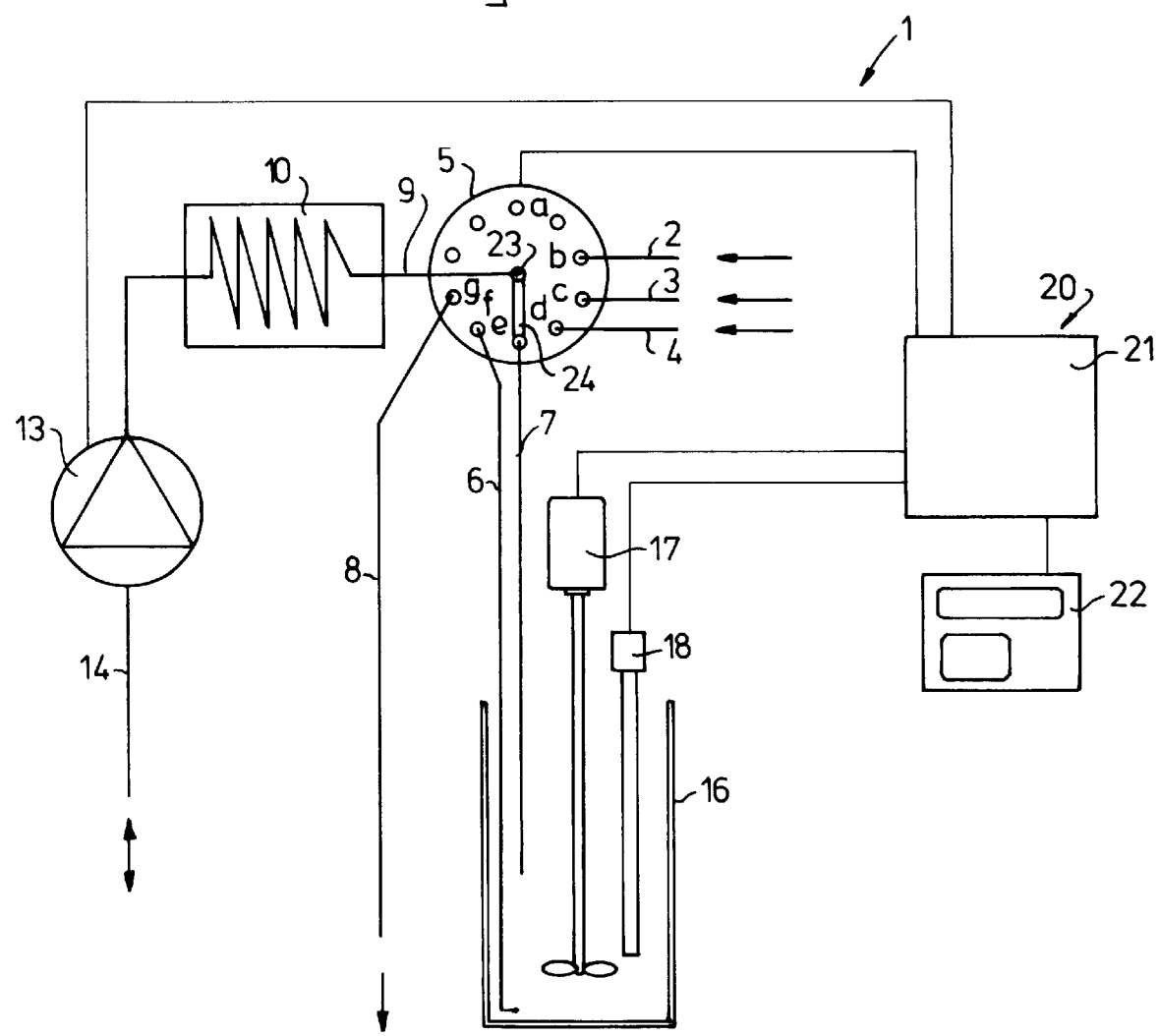
FIG. 1 shows a diagrammatic overview of a first embodiment of an analysis device according to the present invention, with the feed line for the reactant opening into the pump.

FIG. 1 shows an analysis device 1 comprising feed lines 2, 3, 4 which are connected to a analysis valve 5. The device 1 comprises two separate discharge liens 6, 7, as well as a flushing line 8, which are also connected to the analysis valve 5. A pump line 9, in which there is a storage member 10, is accommodated between the multi-way valve 5 and a pump 13. A feed line 14 for a reactant is connected to the suction side of the pump 13.

The discharge lines 6 and 7 open into an analysis or reaction vessel 16, in which there is an agitator 17 and a sensor 18. The multi-way valve 5, the pump 13, the agitator 17 and the sensor 18 are controlled via an operating device 20 comprising a microprocessor 21 and an input unit 22.

Via the feed lines 2, 3 and 4, an auxiliary liquid, a rinsing agent or a sample to be analysed, respectively, can be fed to the pump line 9 and to the storage container 10. To this end, a central opening 23 of the multi-way valve 5 is connected, via the connecting channel 24 arranged in a rotatable shut-off valve, to one of the openings b, c or d of the valve 5. The pump 13 is performing a sucking action. Then, the liquid held in the storage container or storage coil 10 can be fed, via the first discharge line 6, to the analysis vessel 16 by connecting the central opening 23 to the openings e or f of the multi-way valve 5. The pump 13 is performing a pumping action.

Then, the central channel 24 can be connected to the opening g of flushing line 8 and the storage container 10 can be filled with reactant, such as titrant, which is fed from the feed line 14 to the storage container 10 under pumping action of the pump 13. The remaining auxiliary liquid or sample to be analysed is discharged from the storage container 10 via the flushing line 8. Then, the channel 24 can be connected to the opening f of the multi-way valve 5 and the titrant can be delivered in a metered manner, via the second discharge line 7, to the analysis vessel 16. Feeding titrant via the second discharge line 7, which is separate from the discharge line 6 for feeding the sample to be analysed, prevents cross-contamination. It is clear that the sample may also be fed via the discharge line 7 while the titrant is supplied to the analysis vessel 16 via the line 6.

A titration can be carried out as follows under the control of the operating device 20.

Initially, the connections between the pump 13 and the storage container 10, for example hose connections, as well as the valve 5 are filed with titrant. The discharge line 7 is always filled with titrant. Via the line 4, with the central channel 24 connection position d of the valve 5 to the central opening 23, a quantity of sample, which is such that the sample does no reach the pump 13, is drawn into the storage container 10. The volume of the storage container, for example a storage coil, needs to be sufficiently large for this to be achieved. It is also necessary to take into account the fact that the titrant and the sample disperse into one another at a contact surface during transport through the lines. If appropriate, one or more reagents, as auxiliary liquids, may be drawn up in an analogous manner via the line 2 by rotating the valve 5 in such a manner that the central channel 24 is connected to the opening b. After the sample and any auxiliary liquids have been introduced into the storage container 10, they are transferred to the reaction vessel 16 by switching the valve 5 into position f and by metering a predetermined volume into the vessel 16 by means of the pump 13. Any rinsing liquid which is present in the discharge line 7 also passes into the reaction vessel 1 but does not have any effect on the analysis. The quantity of sample which is metered into the analysis vessel 1 in this way is less than the previously drawn-in quantity of sample and reagent together, so that titrant is prevented from passing into the line 7 or into the analysis vessel 16. Then, the rest of the sample is discharged via the flushing line 8 by connecting the central channel 24 to opening g of the valve 5. In this case, sufficient titrant is fed to the flushing lie 8 by the pump 13 for the valve 5 to be completely filled with titrant. Finally, the valve 5 is switched in such a manner that the central channel 24 is connected to the feed line 6, after which titration can be begun with the aid of the agitator 17 and the sensor 18 by controlling the microprocessor system 21 in a manner which is known per se, as described in the introduction. After the titration is complete, the analysis vessel 16 is emptied and flushed in order to ensure a high level of accuracy during the next analysis. To this end, the contents of the analysis vessel 16 are drawn into the line 6. In order to remove all the liquid from the valve vessel 16, the end of the line 6 reaches down to the bottom of the vessel. The entire contents of the vessel are now drawn up past the valve 5. Here too, it is important that the reaction mixture does not reach the pump 13. To this end, the volume of the storage container 10 is selected in such a manner that it at least corresponds to the volume of the analysis vessel 16. Then, the contents of the storage container 10 are discharged via the flushing line 8. In order to flush the analysis vessel 16, a volume of rinsing liquid is drawn into the storage container 10 via the line 3 and is then introduced into the analysis vessel 16 via the discharge line 6. In this case, the metered volume of rinsing liquid should be less than the volume of rinsing liquid drawn in, in order to prevent titrant from passing into the analysis vessel 16. The flushing action is assisted further by stirring the rinsing liquid for a period of time in the analysis vessel 16 using agitator 18. Finally, the rinsing liquid is drawn back out of the analysis vessel through the discharge line 6 and is removed via the flushing line 8. The analysis device is then back in its initial situation and is ready to carry out the next analysis.

Instead of a bidirectional pump 13, it is also possible to use a piston pump or a plunger burette 25, as shown in FIG. 2. As can be seen from FIG. 2, the burette 25 does not have to have an additional valve in order to be able to be filled. Via the feed line 26 which opens into the opening a of the multi-way valve 5, a stock or titrant can be fed to the burette 25. In this case, a reservoir 29 for storing titrant is formed between the piston 27 and the housing 28 of the burette. The burette 25 could be filled at the instant after the sample has been metered into the analysis vessel 16 and the remainder of the sample has been removed from the storage container 10 via the flushing line 8, so that the valve 5 is filled with titrant. The rest of the action of the device in accordance with FIG. 2 is similar to that described with regard to FIG. 1.

In the analysis device according to the present invention, the pump, system of lines and multi-way valve may be designed as separate components. However, it is also possible to form these components as a single part made, for example, of metal. Furthermore, the storage container 10 is not limited to a storage coil, but may also adopt other similar forms, such as for example a simple reservoir or a widening in the diameter of the pump line 9. Furthermore, the multi-way valve 5 may be formed by a selector valve which is known per se, but may also comprise other designs.

What is claimed is:

1. An analysis device (1) comprising:

an analysis vessel (16);

only a single pump (13, 25);

a multi-way valve (5) connected to said pump via a pump line (9);

a storage member (10) positioned in said pump line intermediate said multi-way valve and said pump;

a first discharge line (6) and a second discharge line (7), both of said first and second discharge lines connected to said multi-way valve and connectable to said analysis vessel;

a first feed line (4) connected to said multi-way valve, for feeding a sample to be analyzed to said multi-way valve;

a second feed line (14, 26) connected to said multi-way valve or to said pump for feeding a reactant to said multi-way valve;

a flushing line (8) connected to said multi-way valve;

an operating device (20) operatively connected to and controlling said pump and said multi-way valve, said multi-way valve being configurable to place said first and second discharge lines, said first feed line, and said flushing line in fluid communication with said pump line via said multi-way valve, wherein no other elements but said storage member are positioned in said pump line for receiving the sample to be analyzed, and wherein said operating device is designed and operable to successively receive the sample in said storage member, transfer the sample, via said first discharge line, from said storage member into said analysis vessel and transfer the reactant, via said second discharge line, into said analysis vessel.

2. Analysis device (1) according to claim 1, characterized in that the second feed line (14) for the reactant opens into the pump (13) and, via the pump and the pump line (9), can be placed in fluid communication with the multi-way valve (5).

3. Analysis device (1) according to claim 1, characterized in that the second feed line (26) for the reactant opens into the multi-way valve (5), the pump (25) comprising a storage reservoir (29) for the reactant.

4. Analysis device (1) according to claim 1, characterized in that the storage member (10) comprises a coil-shaped line part.

5. Analysis device (1) according to claim 1, characterized in that the multi-way valve (5) comprises a central opening (23), the pump line (9) opening into the central opening (23), a multiplicity of openings (a, b, c, d, e, f, g), which are connected to the respective feed and discharge lines and to the flushing line and are situated at a distance from the central opening (23), as well as a rotatable shut-off valve with a connecting channel (24), which is connected to the central opening (23) and can be connected, by rotating the shut-off valve, to each of the openings (a–g) which are situated at a distance from the central opening.

6. Analysis device according to claim 1, characterized in that the pump (13, 25) is a bidirectional pump.

7. Analysis device according to claim 1, characterized in that the operating device (20) is designed to carry out the following steps:

a. connecting the first feed line (4) to the pump line (9) via the multi-way valve (5), b. using the pump (13, 25) to suck the sample into the storage member (10), c. connecting the pump line (9) to the first discharge line (6) via the multi-way valve (5), d. feeding some of the sample present in the storage member (10) to the analysis vessel (16) via the pump (13, 25) and via the first discharge line (6), e. connecting the pump line (9) to the flushing line (8) via the multi-way valve (5), f. discharging sample which has remained in the storage member (10) via the flushing line (8) by feeding the reactant to the multi-way valve (5) until the multi-way valve (5) is full of reactant, g. connecting the pump line (9) to the second discharge line (7) via the multi-way valve (5), and h. introducing the reactant into the analysis vessel (16) via the second discharge line (7).

* * * * *